United States Patent [19]
Bryson

[11] 4,096,994
[45] Jun. 27, 1978

[54] MANUAL DEODORIZER DISPENSER

[75] Inventor: John D. Bryson, Milwaukee, Wis.

[73] Assignee: Will Ross, Inc., Milwaukee, Wis.

[21] Appl. No.: 761,544

[22] Filed: Jan. 21, 1977

[51] Int. Cl.$^2$ ............................................... A61L 9/04
[52] U.S. Cl. ....................................... 239/57; 239/59; 222/482
[58] Field of Search .................................. 239/57–59; 222/142.4, 482, 552; 229/7 R, 17 R

[56] References Cited

U.S. PATENT DOCUMENTS

| | | | |
|---|---|---|---|
| 2,072,432 | 3/1937 | Solomon | 222/482 X |
| 2,500,896 | 3/1950 | Drake | 239/59 X |
| 2,547,688 | 4/1951 | Brody | 239/57 |
| 3,790,081 | 2/1974 | Thornton et al. | 239/59 X |
| 3,885,737 | 5/1975 | Watkins | 239/34 |

FOREIGN PATENT DOCUMENTS 2,231,216  12/1974  France .................................. 239/59

Primary Examiner—Robert W. Saifer
Attorney, Agent, or Firm—Michael, Best & Friedrich

[57] ABSTRACT

Disclosed herein is a dispenser comprising a housing having opposed first and second end walls each having therein respective parts rupturable from the end walls to provide respective first and second apertures, a first valve member mounted on the housing for movement relative to the first end wall between positions operative, when the first end wall is ruptured, to open and close the first aperture, a second valve member mounted on the housing for movement relative to the second end wall between positions operative, when the second end wall is ruptured, to open and close the second aperture, a plurality of spaced legs extending integrally from the first valve member in a direction extending away from the housing and adapted to support the housing in upright position on a supporting surface, to facilitate manual movement of the first valve member, and to afford flow of air between the legs and through the apertures and the housing after rupture of the end walls and when the valve members are in the open positions, and a container located in the housing and containing a substance which is to be dispensed in response to air flow through the housing.

21 Claims, 3 Drawing Figures

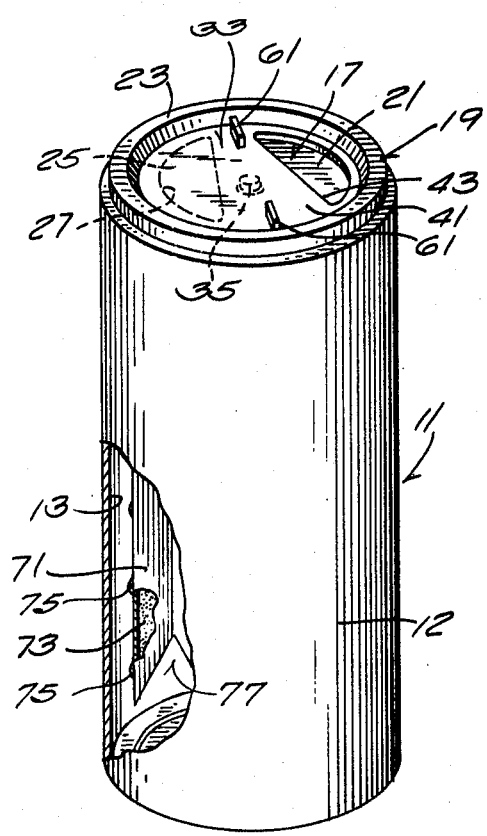
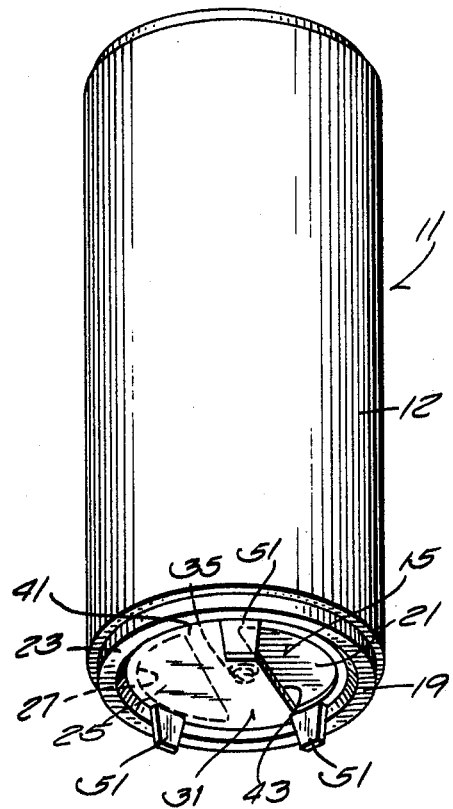
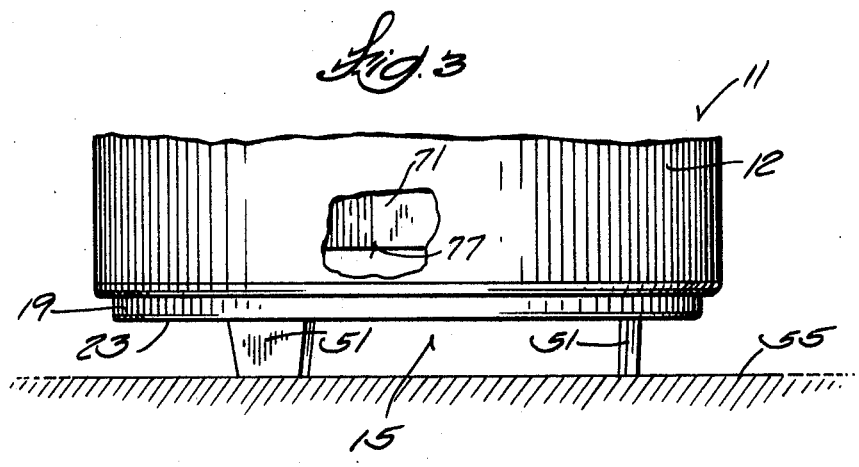

MANUAL DEODORIZER DISPENSER

BACKGROUND OF THE INVENTION

The invention relates generally to dispensers for agents such as deodorants, odorants, insecticides and the like.

More particularly, the invention relates to dispensers such as are shown in the following United States Patents:

| Wilhelm | 2,038,071 | issued April 21, 1936 |
| Drake | 2,500,896 | issued March 14, 1950 |
| Thornton | 3,790,081 | issued Feb. 5, 1974 |

SUMMARY OF THE INVENTION

The invention provides a dispenser comprising a housing having a first end wall having therein a first aperture, a second aperture spaced from the first end wall, a first valve member mounted on the housing for movement relative to the first end wall between positions operative, when the first end wall is ruptured, to open and close the first aperture, a second valve member mounted on the housing for movement relative to the second end wall between positions operative, when the second end wall is ruptured, to open and close the second aperture, a plurality of spaced legs extending integrally from the first valve member in a direction extending away from the housing and adapted to support the housing in upright position on a supporting surface, to facilitate manual movement of the first valve member, and to afford flow of air between the legs and through the apertures and the housing after rupture of the end walls and when the valve members are in the open positions, and a container located in the housing and containing a substance which is to be dispensed in response to air flow through the housing.

Also in accordance with the invention, the housing is so constructed so as to be substantially air tight and impermeable to the substance to be dispensed when the valve members are in the closed positions.

In accordance with an embodiment of the invention, the first end wall includes an outwardly extending peripheral flange including an end surface and an inner generally planar main portion having therein the aperture, and the legs extend from the first valve member beyond the end surface of the flange so that when the dispenser is stood upright on the legs, the end surface is elevated with respect to the surface supporting the legs.

In accordance with an embodiment of the invention, the first valve member is rotatable relative to the first end wall and the plurality of legs comprises three legs spaced radially from and equiangularly about the axis of rotary movement between the first valve member and the first end wall.

In accordance with an embodiment of the invention, the main portion of the first end wall includes a part which is at least partially severable therefrom to provide the first aperture and the first valve member includes means defining an open part which is in registry with the first aperture when the first valve member is in the open position and which is fully out of registry with the first aperture when the first valve member is in the closed position.

In accordance with an embodiment of the invention, the second valve member includes a projection affording manual manipulation of said second valve member between the open and closed positions.

One of the principal features of the invention is the provision of a dispenser including a housing which is substantially air-tight and impermeable to the substance to be dispensed and which includes opposed end walls which are rupturable, together with movable valve members which cooperate with the ruptured end walls to provide valves, with one of the movable valve members integrally including a plurality of legs which facilitate manual manipulation of the one valve member between open and closed positions and which additionally facilitate upright positioning of the dispenser on a supporting surface for vertical air flow therethrough and between the legs when the valve members are in the open positions.

Another of the principal features of the invention is the provision of a dispenser which is relatively economical to construct.

Other features and advantages of the embodiments of the invention will become known by reference to the following general description, appended claims, and drawings.

THE DRAWINGS

FIG. 1 is a top perspective view, partially broken away, illustrating a dispenser embodying various of the features of the invention.

FIG. 2 is a bottom perspective view of the dispenser shown in FIG. 1.

FIG. 3 is a fragmentary elevational view of the lower portion of the dispenser shown in FIG. 1, when the dispenser is standing upright on a supporting surface.

Before explaining the embodiments of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein is for the purposes of description and should not be regarded as limiting.

GENERAL DESCRIPTION

Shown in the drawings is a dispenser 11 including a housing 12 which can be of any desired shape, which includes a hollow chamber or interior 13 and which, in the illustrated construction includes an outer wall which is of elongated cylindrical shape and is fabricated of paperboard and aluminum foil. The housing 12 is closed at its opposed spaced ends by first and second or bottom and top end walls 15 and 17 which, in the illustrated construction, are fabricated of impermeable plastic and respectively each includes raised and outwardly axially extending peripheral flanges 19 and recessed or axially inner generally planar main portions 21.

The flanges 19 each includes an outer end surface 23 and the main end wall portions 21 each includes a part 25 which, at least in part, is rupturable or severable from the remainder of the main portion 21 and displaceable relative to the main end wall portion 21 to provide therein an aperture 27. Prior to rupture or severance of the part 25 of the main end wall portion 21, the interior 13 of the housing 12 is substantially air-tight.

Movably mounted on the housing 12, at each of the ends thereof, are respective first and second or bottom and top valve members 31 and 33 which, in the illustrated construction, are fabricated of plastic. The valve members 31 and 33 are pivotally or rotatably mounted to the end walls 15 and 17 by cylindrical studs or projections 35 which extend through centrally located openings in the main portions 21 of the end walls 15 and 17 and which are then suitably enlarged by the application of heat or otherwise to prevent disassembly of the valve members 31 and 33 from the end walls 15 and 17, to maintain the valve members 31 and 33 in closely adjacent relation to the generally planar main portions 21 of the end walls 15 and 17, and to permit rotation of the valve members 31 and 33 relative to the associated end walls 15 and 17.

Each of the valve members includes a main body 41 which is generally of planar construction and which has a notch or cut out part 43 which can be of the same size and shape as the corresponding aperture 27 in the associated end wall and which, incident to valve member rotation relative to the associated end wall, is movable between a closed position in which the valve member main body 41 totally closes or shuts off the aperture in the associated end wall and an open position in which the notch or cut out part 43 is in registry with the aperture in the adjacent end wall so as to permit air flow therethrough and relative to the interior of the housing 12.

Extending from the main body 41 of the bottom valve member 31 are a plurality of spaced projections or legs 51 which are adapted to support the dispenser 11 in an upright position on a supporting surface 55, which constitutes means enabling easy manual manipulation of the bottom valve member 31 to rotate the bottom valve member 31 relative to the associated end wall 15, and which, when the valve members 31 and 33 are in the open positions, afford flow of air between the legs 51 and between the supporting surface 55 and the end surface 23 for travel relative to the interior chamber 13 of the housing 12 and relative to the aperture 27 in the top end wall 17. While other constructions are possible, in the illustrated construction, three equi-angularly spaced legs 51 are provided adjacent the periphery of the bottom valve member 31, which legs 51 have a length in the direction of the axis of the housing 12 of sufficient length to extend beyond the end surface 23 of the bottom end wall flange 19 and to support the bottom end wall flange 19 in spaced relation above the supporting surface 55.

The top valve member 33 also includes one or more projections 61 which facilitate manual manipulation of the top valve member 33 between its open and closed positions. Preferably, the projection or projections 61 terminate short of the end surface 23 of the top end wall flange 19.

Contained within the interior chamber 13 of the housing 12 is an envelope or package 71 including at least one flexible wall of plastic material. Contained within the envelope 71 is an agent or substance 73 to be dispensed, which substance is permeable through the plastic wall of the envelope 71. The substance can be an insecticide or an odorant or a deodorant or other like composition which is permeable through the flexible wall of the envelope or package 71. In particular, the dispenser contemplates the use of a package or envelope such as are disclosed in U.S. Pat. Nos. 3,785,556 issued Jan. 15, 1974 and 3,885,737 issued May 27, 1975 incorporated herein by reference. Preferably a part or edge of the package is secured to the housing by suitable means, such as a glue 75, to hold the package in spaced relation from the end walls to thereby provide plenums 77 adjacent both the bottom and top end walls 15 and 17. Other arrangements for containing or storing agents or substances to be dispensed can also be employed within the interior chamber 13 of the housing 12.

The elongated cylindrical wall of the housing is constructed so as to be air-tight and, in addition, in order to prevent loss therethrough to the atmosphere of the substance to be dispensed at times other than when desired, the elongated cylindrical wall of the housing is coated or lined or otherwise treated or fabricated so as to prevent permeation therethrough of the substance to be dispensed. Such treatment or fabrication can include application to the elongated wall of materials which are impermeant to the substance to be dispensed. For instance, one or more of the surfaces of the elongated wall can be sprayed or coated with a film of polypropylene. Alternatively, a film of polypropylene or of aluminum or of mylar or other like material can be laminated to the paperboard of the elongated wall so as to prevent permeation therethrough of the substance to be dispensed and so as to insure that the outer wall is air-tight.

Also in order to render the housing airtight and impermeant to the substance to be dispensed, the end wall components are constructed of plastic material which is impervious to the substance to be dispensed, such as, for instance, polypropylene or ABS copolymers, a generic term for copolymers made from acrylonitrile, butadiene, and styrene which are light in weight and resistant to chemicals and tensile stress. In addition, the end walls are assembled to the elongated wall at the ends thereof so as to maintain the air-tight integrity of the housing and so as to prevent unwanted passage therethrough of the substance to be dispensed.

When the valve members 31 and 33 are in their closed positions, the air-tight condition of the interior chamber 13 of the housing 12 is substantially maintained so as to prevent loss from the housing 12 of the agent or substance which can be dispensed therefrom.

In use, the dispenser 11 is placed upright with the legs 51 supporting the dispenser 11 on the surface 55. When in the upright condition, the valve members 31 and 33 can be located so as either to open or close the apertures 23 in the associated end walls 15 and 17. In this last regard, it is pointed out that the dispenser supporting legs 51 which project from the bottom valve member 31 can also be employed to rotate the bottom valve member 31 so as to selectively locate the cut out part or notch 43 either in registry or out of registry with the aperture 27 and thereby either open or close the aperture 27 in the bottom end wall 15.

In addition, as already pointed out, the legs 51 extend integrally from the bottom valve member 31 and have sufficient height or length so as to locate the end surface 23 of the bottom end wall flange 19 above the supporting surface 55 and to permit air flow under the bottom end wall 15 and above the supporting surface 55 and between the legs 51 and relative to the aperture 27 so as to thereby afford flow through interior chamber 13 of the housing 12 and relative to the top end wall aperture 27 when the upper valve member 33 is suitably positioned.

Various of the features of the invention are set forth in the following claims.

What is claimed is:

1. A dispenser comprising a housing having a first end wall having therein a first aperture, a second aperture spaced from said first end wall, a first valve member mounted on said housing for movement relative to said first aperture between a position closing said first aperture and a position opening said first aperture, a second valve member mounted on said housing for movement relative to said second aperture between a closed position closing said second aperture and an open position opening said second aperture, a plurality of spaced legs extending integrally from said first valve member in a direction extending away from said housing and adapted to support said housing in upright position on a supporting surface, to facilitate manual movement of said first valve member, and to afford flow of air between said legs and through said apertures and said housing when said valve members are in said open positions, and a container located in said housing and containing a substance which is to be dispensed in response to air flow through said housing.

2. A dispenser in accordance with claim 1 wherein said housing is substantially air-tight and impermeable to flow of said substance when said valve members are in said closed positions.

3. A dispenser in accordance with claim 2 wherein said first end wall includes an outwardly extending peripheral flange including an end surface and an inner generally planar main portion having therein said first aperture, and wherein said legs extend from said first valve member beyond said end surface of said flange so that when said dispenser is stood upright on said legs, said end surface is elevated with respect to the surface supporting said legs.

4. A dispenser in accordance with claim 3 wherein said first valve member is rotatable relative to said first end wall and wherein said plurality of said legs comprises three legs spaced radially from and equi-angularly about the axis of rotary movement between said first valve member and said first end wall.

5. A dispenser in accordance with claim 4 wherein said main portion of said first end wall includes a part which is at least partially severable therefrom to provide said first aperture and wherein said first valve member includes means defining an open part which is in registry with said first aperture when said first valve member is in the open position and which is fully out of registry with said first aperture when said first valve member is in the closed position.

6. A dispenser in accordance with claim 2 wherein said second valve member includes a projection affording manual manipulation of said second valve member between said open and closed positions.

7. A dispenser in accordance with claim 6 wherein said second end wall includes an outwardly extending peripheral flange including an end surface and an inner generally planar main portion having therein said second aperture, wherein said valve member is mounted for rotation relative to said second end wall, and wherein said projection terminates inwardly of said end surface of said second end wall.

8. A dispenser in accordance with claim 2 wherein said housing is an elongated cylinder.

9. A dispenser in accordance with claim 2 wherein said container includes a flexible plastic wall which is permeant to the substance being dispensed.

10. A dispenser in accordance with claim 9 wherein said substance being dispensed is taken from a group including odorants, deodorants and insecticides.

11. A dispenser comprising a housing having opposed first and second end walls each having therein respective means rupturable from said end walls to provide respective first and second apertures, a first valve member mounted on said housing for movement relative to said first end wall between positions operative, when said first end wall is ruptured, to open and close said first aperture, a second valve member mounted on said housing for movement relative to said second end wall between positions operative, when said second end wall is ruptured, to open and close said second aperture, a plurality of spaced legs extending integrally from said first valve member in a direction extending away from said housing and adapted to support said housing in upright position on a supporting surface, to facilitate manual movement of said first valve member, and to afford flow of air between said legs and through said apertures and said housing after rupture of said end walls and when said valve members are in the open positions, and a container located in said housing and containing a substance which is to be dispensed in response to air flow through said housing.

12. A dispenser in accordance with claim 11 wherein said housing is substantially air-tight and impermeable to flow of said substance when said valve members are in said closed positions.

13. A dispenser in accordance with claim 12 wherein said first end wall includes an outwardly extending peripheral flange including an end surface and an inner generally planar main portion having therein said first aperture, and wherein said legs extend from said first valve member beyond said end surface of said flange so that when said dispenser is stood upright on said legs, said end surface is elevated with respect to the surface supporting said legs.

14. A dispenser in accordance with claim 13 wherein said first valve member is rotatable relative to said first end wall and wherein said plurality of said legs comprises three legs spaced radially from and equi-angularly about the axis of rotary movement between said first valve member and said first end wall.

15. A dispenser in accordance with claim 14 wherein said first valve member includes means defining an open part which is in registry with said first aperture when said first valve member is in the open position and which is fully out of registry with said first aperture when said first valve member is in the closed position.

16. A dispenser in accordance with claim 12 wherein said second valve member includes a projection affording manual manipulation of said second valve member between said open and closed positions.

17. A dispenser in accordance with claim 16 wherein said second end wall includes an outwardly extending peripheral flange including an end surface and an inner generally planar main portion having therein said second aperture, wherein said valve member is mounted for rotation relative to said second end wall, and wherein said projection terminates inwardly of said end surface of said second end wall.

18. A dispenser in accordance with claim 12 wherein said housing is an elongated cylinder.

19. A dispenser in accordance with claim 12 wherein said container includes a flexible plastic wall which is permeant to the substance being dispensed.

20. A dispenser in accordance with claim 19 wherein said substance being dispensed is taken from a group including odorants, deodorants and insecticides.

21. A dispenser for dispensing a substance, said dispenser comprising an elongated, cylindrical housing having opposed first and second end walls respectively including an outwardly extending peripheral flange including an end surface and an inner generally planar main portion including therein a part which is at least partially severable therefrom to provide respective first and second apertures in said first and second end walls, a first valve member mounted on said housing for rotary movement relative to said first aperture between a position closing said first aperture and a position opening said first aperture, said first valve member including means defining an open part which is in registry with said first aperture when said first valve member is in the open position and which is out of registry with said first aperture when said first valve member is in the closed position, a second valve member mounted on said housing for rotary movement relative to said second aperture between a position closing said second aperture and a position opening said second aperture, said second valve member including means defining an open part which is in registry with said second aperture when said second valve member is in the open position and which is out of registry with said second aperture when said second valve member is in the closed position, said housing being substantially air-tight and impermeable to the substance when said valve members are in said closed positions, a projection extending integrally from said second valve member and affording manual manipulation of said second valve member between the open and closed positions, said projection terminating inwardly of said end surface of said second end wall, a plurality of spaced legs extending integrally from said first valve member in a direction extending away from said housing and beyond said end surface of said first end wall and so as to facilitate support of said housing in upright position on a supporting surface with said end surface of said first end wall in elevated relation with respect to the surface supporting said legs, to facilitate manual manipulation of said first valve member between the open and closed positions, and to permit flow of air between said legs and through said apertures and said housing when said valve members are in said open positions and said housing is supported in upright position on the supporting surface, and a container located in said housing and containing a substance which is to be dispensed in response to air flow through said housing, said container including a flexible plastic wall which is permeant to said substance being dispensed, and said substance being dispensed being taken from a group including odorants, deodorants, and insecticides.

* * * * *